US00PP14938P2

(12) United States Plant Patent
Mowrey et al.

(10) Patent No.: US PP14,938 P2
(45) Date of Patent: Jun. 22, 2004

(54) PLUM TREE NAMED 'SUPLUMTWENTYEIGHT'

(50) Latin Name: *Prunus salicina*
Varietal Denomination: Suplumtwentyeight

(75) Inventors: Bruce D. Mowrey, Watsonville, CA (US); David W. Cain, Bakersfield, CA (US); Terry A. Bacon, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 0 days.

(21) Appl. No.: 10/463,793

(22) Filed: Jun. 16, 2003

(51) Int. Cl.[7] ..... A01H 5/00
(52) U.S. Cl. ..... Plt./184
(58) Field of Search ..... Plt./184

(56) References Cited

U.S. PATENT DOCUMENTS

PP4,902 P 10/1982 Weinberger

*Primary Examiner*—Bruce R. Campell
*Assistant Examiner*—W C Haas
(74) *Attorney, Agent, or Firm*—Knobbe, Martens, Olson & Bear, LLP

(57) ABSTRACT

A new and distinct plum variety that possesses heavy and consistent production of large, firm, black skinned, early-ripening fruit of excellent eating quality. The juicy flesh develops a red color upon ripening.

1 Drawing Sheet

Latin name of the genus and species of the plant claimed: *Prunus salicina*.

Variety denomination: 'Suplumtwentyeight'.

BACKGROUND AND SUMMARY OF THE INVENTION

This invention relates to the discovery and asexual propagation of a new and distinct variety of plum tree, herein after referred to by the cultivar name 'Suplumtwentyeight'. The variety originated by hybridization performed by Bruce Mowrey. The new variety was first selected and evaluated by David Cain on Sun World Experimental Ranch 75 near Wasco, Calif. in Kern County. The new variety is characterized by heavy and consistent production of large (65 mm diameter), firm fruit that ripens early, during the middle of June in the Bakersfield, Calif. area. Fruit of 'Suplumtwentyeight' have smooth black-colored skin and flesh that develops red color as they ripen. Eating quality is excellent with 18° brix, plentiful juice, and skin flavor that is neutral.

The parent varieties were first crossed in 1993, with the date of planting of February, 1994, and the date of first flowering being March, 1997. The new plum variety was first asexually propagated by Terry Bacon near Wasco, Kern County, Calif. in December, 2001, by grafting onto Nemaguard rootstock.

The seed parent is Sun World breeding selection, '91P-001' (unpatented), which was selected from a progeny of Sun World breeding selection '232-205' (unpatented) crossed with pollen from Sun World selection '275-*136*' (unpatented). The new variety is distinguished from its seed parent by ripening 16 days later and having fruit that averages 65 mm as compared to '91P-001' with 55 mm. Additionally, the new variety develops red flesh as it ripens while '91P-001' has amber flesh. The pollen parent was an unknown Sun World breeding selection.

The new variety most nearly resembles 'Suplumeleven' (U.S. Plant Pat. No. 4,902). It may be distinguished from 'Suplumeleven' by ripening 20 days earlier. The new variety ripens approximately the same time as 'Santa Rosa' (unpatented) but develops red flesh while 'Santa Rosa' has amber-colored flesh, and is larger (65 mm compared to 55 mm diameter with 'Santa Rosa').

The new plum tree variety cv. 'Suplumtwentyeight' has been shown to maintain its distinguishing characteristics.

BRIEF DESCRIPTION OF THE FIGURE

The accompanying color photographic illustration in FIG. 1 shows typical specimens of the foliage and fruit of the new plum variety. The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED BOTANICAL DESCRIPTION OF THE INVENTION

Figure 1:
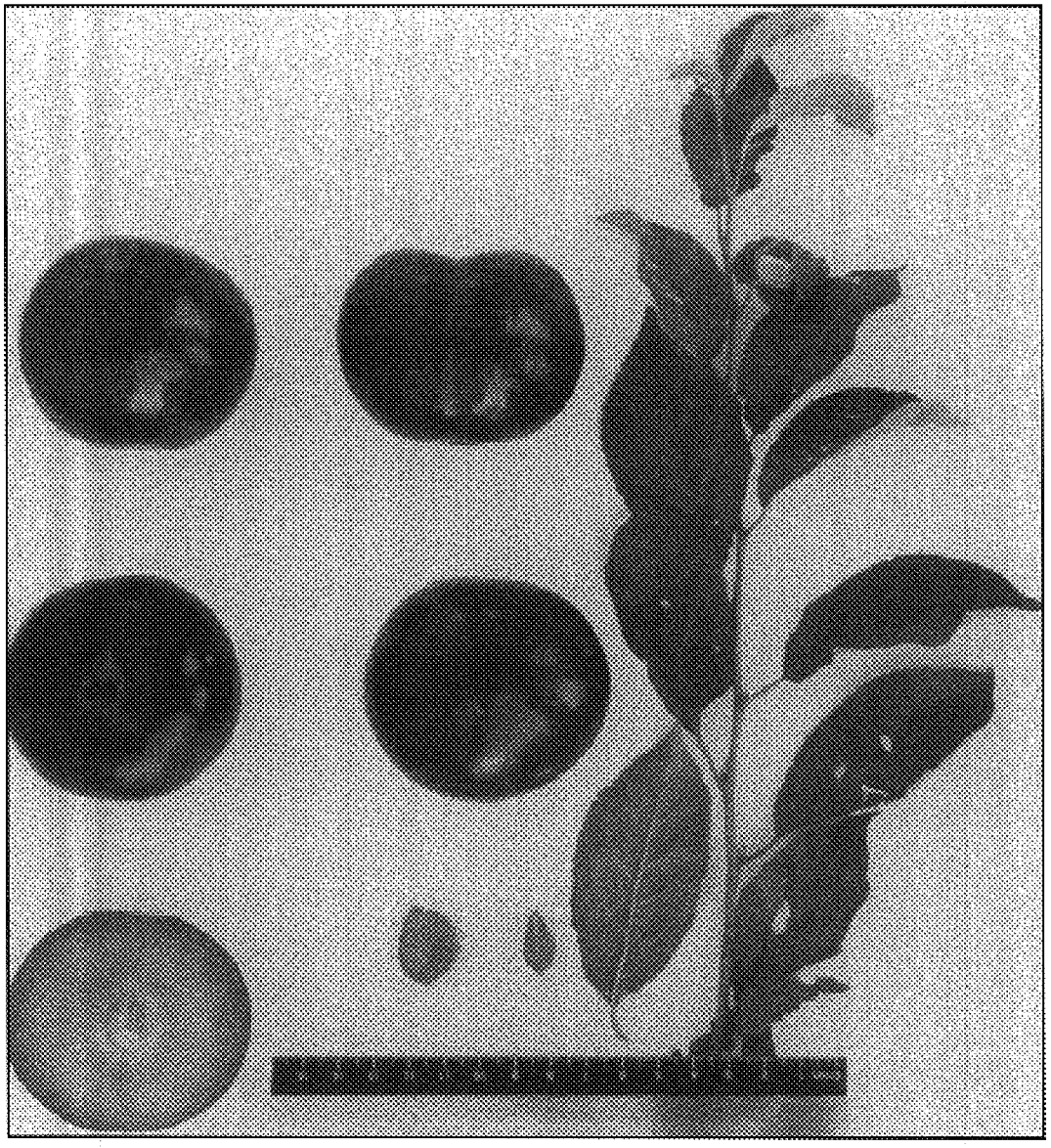

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

The descriptive matter which follows pertains to 8 year old trees grown in the vicinity of Wasco, Kern County, Calif., during 2002, and is believed to apply to plants of the variety grown under similar conditions of soil and climate elsewhere.

TREE (Measurements Taken on an 8 Year Old Tree)

General:

*Size.*—Medium — normal for most plum varieties. Reaches a height of approximately 3–4 meters including normal pruning.

*Vigor.*—Vigorous; Growth of approximately 1.8 to 2 meters height the first growing season.
*Growth.*—Upright-spreading.
*Productivity.*—Productive. Fruit set is usually two or more times desired amount for marketable size fruit. Thinning and spacing of fruit is necessary.
*Form.*—Vase formed.
*Fruit bearing.*—Regular. No alternate bearing observed.
*Fertility.*—Somewhat self-fertile but pollinizer improves fruit set.
*Density of foliage.*—Dense. Pruning is required to open tree vase shape, allowing more sunlight to center of tree.
*Hardiness.*—Hardy in all fruit growing areas of California. Winter chilling requirement is approximately 650 hours at or below about 7.2° C.
*Tree resistance/susceptibility.*—No specific testing for relative plant disease resistance/susceptibility has been designed. Under close observation in Kern County, Calif., no particular plant/fruit disease resistance/susceptibility has been observed.
*Root stock.*—Nemaguard.

Trunk: (Measurements at 30 cm above soil line).
*Diameter.*—Approximately 20 cm. Varies with soil type, fertility, climatic conditions and cultural practices.
*Surface texture.*—Medium shaggy, increases with age of tree.
*Color.*—About Greyed-orange 164B in recesses of the bark, and about Greyed-green 197A to Greyed-green 196A on the surface of the bark. Becomes darker with age.

Branches: (Measurements at 90 cm above soil line).
*Diameter.*—Ranges from approximately 8.0 cm to 9.0 cm.
*Surface texture.*—Smooth on 1st year wood, increasing roughness with tree age.
*Color.*—Branches are about Greyed-orange 164B in recesses of the bark, and about Greyed-green 197C to Greyed-green 198D on the surface of the bark.

Branch lenticels:
*Number.*—Absent.

LEAVES (Data Taken in July on Fully Expanded Leaf at Midpoint of Current-Season Growth)

General:
*Average length.*—Approximately 90 mm.
*Average width.*—Approximately 35 mm.
*Form.*—Broadly elliptic.
*Leaf blade tip.*—Cuspidate.
*Leaf base.*—Rounded to cuneate.
*Margin.*—Strongly crenate.
*Venation.*—Pinnately net veined.
*Leaf thickness.*—Medium.
*Color of upper surface.*—About Green 139A.
*Color of lower surface.*—About Green 137C.
*Surface texture.*—Smooth.

Petiole:
*Length.*—Approximately 12 mm.
*Diameter.*—Approximately 1.5 mm.
*Color.*—About Green 138B.

Leaf Glands:
*Average number.*—Approximately 2.
*Positioning.*—Opposite on upper portion of petiole and base of leaf blade.
*Length.*—Approximately 0.8 mm.
*Width.*—Approximately 0.8 mm.
*Shape.*—Globose.
*Color.*—About Greyed-orange 165A.

Stipules:
*Number of stipules per bud.*—Approximately 2.
*Length.*—Approximately 4 to 6 mm.

Flowering shoots: (Data taken in July at midpoint of current-season growth).
*Diameter.*—Approximately 4 mm.
*Color.*—About Greyed-orange 165A.
*Size.*—Average.
*Flowering shoot lenticels.*—Plentiful.

Flowering shoot leaf buds:
*Shape.*—Ovoid.
*Length.*—Approximately 2 mm.
*Width.*—Approximately 2 mm.
*Color.*—About Greyed-orange 165A.

Flowering shoot flower buds:
*Number per node.*—Approximately 2 to 4.
*Shape.*—Ovoid.
*Length.*—Approximately 2 mm.
*Width.*—Approximately 2 mm.
*Color.*—About Greyed-orange 175B.

FLOWERS

General:
*Date of first bloom.*—Mar. 1, 2002.
*Date of full bloom.*—Mar. 4, 2002.
*Size (diameter of the fully open flower).*—Approximately 28 mm.
*Flower aroma.*—Very slight.

Peduncle:
*Length.*—Approximately 3 mm.
*Diameter.*—Approximately 1 mm.
*Color.*—About Yellow-green 145A.

Petals:
*Number per flower.*—5.
*Arrangement.*—Slightly overlapping.
*Length.*—Approximately 14 mm.
*Width.*—Approximately 12 mm.
*Shape.*—Circular.
*Apex.*—Rounded.
*Base shape.*—Narrows at point of attachment.
*Color (fully opened flower).*—White.
*Surface texture.*—Smooth.
*Margins.*—Smooth.

Sepals:
*Number per flower.*—5.
*Length.*—Approximately 4 mm.
*Width.*—Approximately 4 mm.
*Shape.*—Broad obovate.
*Color.*—About Yellow-green 145A to Yellow-green 144B.
*Surface texture.*—Smooth.

Stamens:
*Number per flower.*—Approximately 32 (typically ranges between 28 and 34).
*Length.*—Approximately 7 mm.
*Filament color.*—White.
*Anther color (just before dehiscence).*—About Greyed-orange 168A.
*Pollen color.*—About Greyed-orange 168A.

Pistil:

*Number of pistils per typical flower.*—Usually one.

*Frequency of supplementary pistils.*—Occasionally two.

*Pistil length.*—Approximately 12 mm.

*Pubescence.*—None.

*Ovary diameter.*—Approximately 2 mm.

*Stigma position in relation to anthers.*—Stigma extends below anthers.

FRUIT

General: (Data taken at firm-ripe stage on mature tree managed to obtain maximum quality under conditions stated above).

*Harvest date of first pick.*—Jun. 16, 2002.

*Harvest date of last pick.*—Jun. 26, 2002.

*Length* (*stem end to apex*).—Approximately 55 mm.

*Diameter in line with suture plane.*—Approximately 62 mm.

*Diameter perpendicular to suture plane.*—Approximately 65 mm.

*Average weight.*—Approximately 155 gm.

*Shape viewed from apex.*—Nearly rounded, symmetrical.

*Shape viewed from side, facing suture.*—Rounded, slightly flattened. Symmetrical.

*Shape viewed from side, perpendicular to suture.*—Rounded, slightly flattened. Symmetrical.

*Fruit apex shape.*—Somewhat flattened.

*Fruit stem-end cavity depth.*—Shallow.

Stem:

*Length.*—Approximately 8 mm.

*Diameter.*—Approximately 2 mm.

*Color.*—About Green 143C.

Skin:

*Thickness.*—Medium.

*Adherence to flesh.*—Tenacious.

*Surface texture.*—Smooth.

*Pubescence.*—None.

*Bloom.*—Moderate amount.

*Ground color.*—Does not show.

*Overcolor.*—About Greyed-purple 187A, becoming black as fruit ripens.

*Taste.*—Neutral.

Flesh:

*Color.*—About Red 36D, becoming about Red 43A from perimeter toward pit cavity as fruit ripens.

*Texture.*—Fine textured and firm.

*Ripens.*—Evenly.

*Fibers.*—Few.

*Flavor.*—Bland-sweet to sweet.

*Aroma.*—Moderate.

*Brix.*—Approximately 18 degrees.

*Juice.*—Plentiful.

*Use.*—Dessert market, local and long distance.

*Keeping and shipping quality.*—Good. Holds well in cold storage for approximately 6 weeks and maintains good firmness and eating quality. Minimal bruising and scarring in packing and shipping trials.

STONE (Measurement Taken on Dried Stones)

General:

*Adherence to flesh.*—Clingstone.

*Length.*—Approximately 21 mm.

*Diameter in line with suture plane.*—Approximately 18 mm.

*Diameter perpendicular to suture plane.*—Approximately 8 mm.

*Form* (*viewed from broad side*).—Obovate. Asymmetrical because of outgrowing keel.

*Form* (*viewed from stem end*).—Oval, symmetrical. Becomes narrow on one side because of outgrowing keel.

*Base shape.*—Flattened to slightly rounded. Retuse at stem attachment.

*Apex shape.*—Rounded with a small dull point.

*Stone surface.*—Irregularly furrowed throughout; heavily ridged throughout; lightly pitted throughout.

*Comparison of stone halves.*—Nearly equal.

*Ridges.*—One on each side of the suture, well formed, sharp, beginning at the base and extending throughout the length of the stone.

*Stone outgrowing keel.*—Well developed.

*Tendency to split.*—None.

*Stone color when dried.*—About Greyed-yellow 161C.

What is claimed is:

1. A new and distinct plum tree named 'Suplumtwentyeight' as herein described and illustrated.

* * * * *